United States Patent
Morgan et al.

[19]

[11] Patent Number: 6,154,673

[45] Date of Patent: Nov. 28, 2000

[54] MULTILINGUAL DEFIBRILLATOR

[75] Inventors: Carlton B Morgan, Bainbridge Island; John F Harris, St. Bellevue, both of Wash.; Cecily Anne Snyder, San Francisco, Calif.; James Daren Bledsoe, Albany, Oreg.; Curtis W Freeman, Windham, N.H.; David A Johnson, Wappingers Falls, N.Y.; Helge Fossan, Stavanger, Norway

[73] Assignees: Agilent Technologies, Inc., Palo Alto, Calif.; Laerdal Medical Corp., Wappinger Falls, N.Y.

[21] Appl. No.: 09/227,480

[22] Filed: Jan. 7, 1999

Related U.S. Application Data

[63] Continuation-in-part of application No. 09/000,807, Dec. 30, 1997, abandoned.

[51] Int. Cl.[7] .................................................. A61N 1/39
[52] U.S. Cl. .................................................. 607/5
[58] Field of Search ............................. 607/4, 5, 6, 9, 607/10, 30, 59

[56] References Cited

U.S. PATENT DOCUMENTS 5,285,792  2/1994  Sjoquist et al. ............................. 607/5
5,652,897  7/1997  Linebarger et al. .
5,693,076  12/1997  Kaemmerer ............................. 607/30
5,749,913  5/1998  Cole .

*Primary Examiner*—George R. Evanisko
*Attorney, Agent, or Firm*—Cecily Anne Snyder

[57] ABSTRACT

This invention relates to an external defibrillator whose language of operation can be easily changed when the defibrillator is deployed for use. Defibrillators include, manual defibrillators, automatic or semi-automatic external defibrillators ("AEDs") and defibrillator trainers. In one embodiment, the invention provides a way to change the language in which the defibrillator delivers instructions to a user. Defibrillators of this invention would contain multiple languages in their memory. During the set-up of the defibrillator some or all of the languages could be designated as a language in which a prompt will be offered. Additionally, during set-up, one language will be designated as the default language. Once the defibrillator is deployed for use in an emergency, the operator will indicate a language preference for the defibrillator operating instructions. Once the user has indicated which language the prompts should be in, the defibrillator will then begin instructing the user in the use of the defibrillator in that language. Conversely, if the user fails to make any language preference indication, the defibrillator will begin instructing the user in the use of the defibrillator in the default language. In an alternate embodiment, the defibrillator issues each instruction in multiple languages.

13 Claims, 8 Drawing Sheets

MULTILINGUAL DEFIBRILLATOR

RELATED APPLICATION

This application is a continuation-in-part of U.S. patent application Ser. No. 09/000,807 filed Dec. 30, 1997, now abandoned.

BACKGROUND OF THE INVENTION

The invention relates to an external defibrillator whose language of operation can be easily changed when the defibrillator is deployed for use. Defibrillators include, manual defibrillators, automatic or semi-automatic external defibrillators ("AEDs"), defibrillator/monitor combinations, advisory defibrillators and defibrillator trainers.

Sudden cardiac arrest ("SCA") most often occurs without warning, striking people with no history of heart problems. It is estimated that more than 1000 people per day are victims of sudden cardiac arrest in the United States alone, which translates into a needless death every 2 minutes.

SCA results when the electrical component of the heart no longer functions properly; this results in an abnormal sinus rhythm. One such abnormal sinus rhythm, ventricular fibrillation ("VF"), is caused by abnormal and very fast electrical activity in the heart. VF may be treated by applying an electric shock to the patient's heart through the use of a defibrillator. The shock clears the heart of abnormal electrical activity (in a process called "defibrillation") by producing a momentary asystole and providing an opportunity for the heart's natural pacemaker areas to restore normal function. If, however, the heart has not been pumping blood for more than 5 minutes, there is an increased likelihood that the victim either will not be resuscitated or will suffer irreversible brain damage. Quick response is therefore necessary. By providing voice and text prompts for the user, the amount of time necessary to review protocols prior to deploying the defibrillator would be reduced.

Over the last several years defibrillators have become more portable and have begun moving into the hands of first responders. As a result, equipment that was once available only in the hospital environment is now being used by police officers, flight attendants and security guards, to name a few, as part of a first-line action in the administration of first aid. The benefit of making this equipment available to the first responders is that it is more likely that a victim of SCA will receive the life saving shock within the first few critical minutes.

Additional information regarding SCA and first aid (including CPR) may be obtained from the American Heart Association internet website at www.amhrt.org. [See, also, Cummins, et al "Improving Survival from Sudden Cardiac Arrest: The 'Chain of Survival' Concept" *Circulation* 83:1832–1847 (1991)].

Currently available external defibrillators often display instructions, status information or other information to assist the defibrillator operator in operating the defibrillator. Some external defibrillators announce such information audibly through a speaker, either in addition to displaying information or instead of displaying information. For example, the FORERUNNER® AED by Heartstream notifies the operator that a shock is advised using both audible and visual prompts and instructs the operator to deliver a shock by pressing the appropriate button. More detailed information directed to defibrillators can be found, for example, in Cameron et al. U.S. Pat. No. 5,607,454 and Cole et al. U.S. Pat. No. 5,611,815.

Prior art defibrillators are typically pre-programmed with a single language for displays or announcements. If a defibrillator programmed for use in one language must be used in a country or region where a potential user speaks a different language, the defibrillator must be reprogrammed to display and/or announce the information in a different language. Such programming and re-programming usually take place before the defibrillator is placed into service, and must take place before the defibrillator is deployed to treat a victim in an emergency. Thus it is necessary to know the language of the defibrillator operator (or user) who will be using a defibrillator prior to making the defibrillator available for use in an emergency.

In another implementation, the Hewlett-Packard CodeMaster defibrillator is provided with multiple languages in memory (typically 9–1). However, the operation language must be selected using the set-up menu which is activated using a three-key combination. Because the set-up menu inactivates the defibrillator operation, language selection is typically performed when the device is placed into service. Once the operation language has been set-up it cannot be changed again without interrupting the defibrillator operation.

In an area, such as Quebec, Canada, where more than one language is commonly spoken, not necessarily with equal proficiency, it would be desirable to have a defibrillator that adapts the language of the prompts in response to the user's indication of language proficiency. There are other geographic areas where such ad hoc language selection would also be beneficial. Additionally, as defibrillators become more commonly available, the need for the defibrillator to be able to communicate with many different potential users, particularly in an ethnically diverse community, will become increasingly important.

Further, it would be desirable to provide a mechanism to change the language of the defibrillator at a later time during operation. For example, if a second tier responder (such as an EMT) arrives who has a different language proficiency than the first tier responder, it would be advantageous to be able to change the operation language of the device without disabling the defibrillator operation.

Many other defibrillators, including manual defibrillators, and defibrillator trainers have been developed and are known in the art, although not discussed herein.

The disclosures of the patents cited herein are incorporated by reference.

What has been needed is a defibrillator where the language of the prompts, either written and/or audible, can be selected by the user at the time that the defibrillator is deployed for use in an emergency. Where the defibrillator is used as a trainer, the language of the prompts are selected by the user when the defibrillator is deployed for use in a simulated emergency, or in the training environment.

SUMMARY OF THE INVENTION

This invention provides an easy way to change the language in a defibrillator at the time the defibrillator is deployed or after the defibrillator is in use.

This invention provides an external defibrillator comprising a controller, and an energy delivery system that is operable by the controller to deliver an electrical shock from an energy source to an electrode interface. The invention further provides an instruction generator which has an input for interacting with the external defibrillator operator to select a language and an instruction generator for providing instructions to a defibrillator operator in a language based on the information from the instruction generator.

The defibrillator may have languages loaded into the memory. The defibrillator may also provide a multiplicity of language selection buttons that enable the user to select a language.

Alternatively, the defibrillator may be programmed to perform all instructions in more than one language. As a result, the defibrillator would operate in a multiplicity of languages sequentially.

This invention is also directed to a method of selecting the operation language of an external defibrillator where a defibrillator operator is prompted to select a language in a first prompting language. Once the defibrillator receives the selection from the operator, the defibrillator determines whether the language is available in memory and then selects the language from the defibrillator's memory. The defibrillator then uses the selected language to provide instructions to the operator.

Further the defibrillator may allow the selected language to be changed, as needed, during the operation of the defibrillator.

The method may also provide for the language to be displayed for selection visually or to be announced audibly. Additionally, the method may provide for additional languages to be displayed for selection visually or to be announced audibly.

DETAILED DESCRIPTION OF THE PREFERRED EMBODIMENTS

Figure 1:
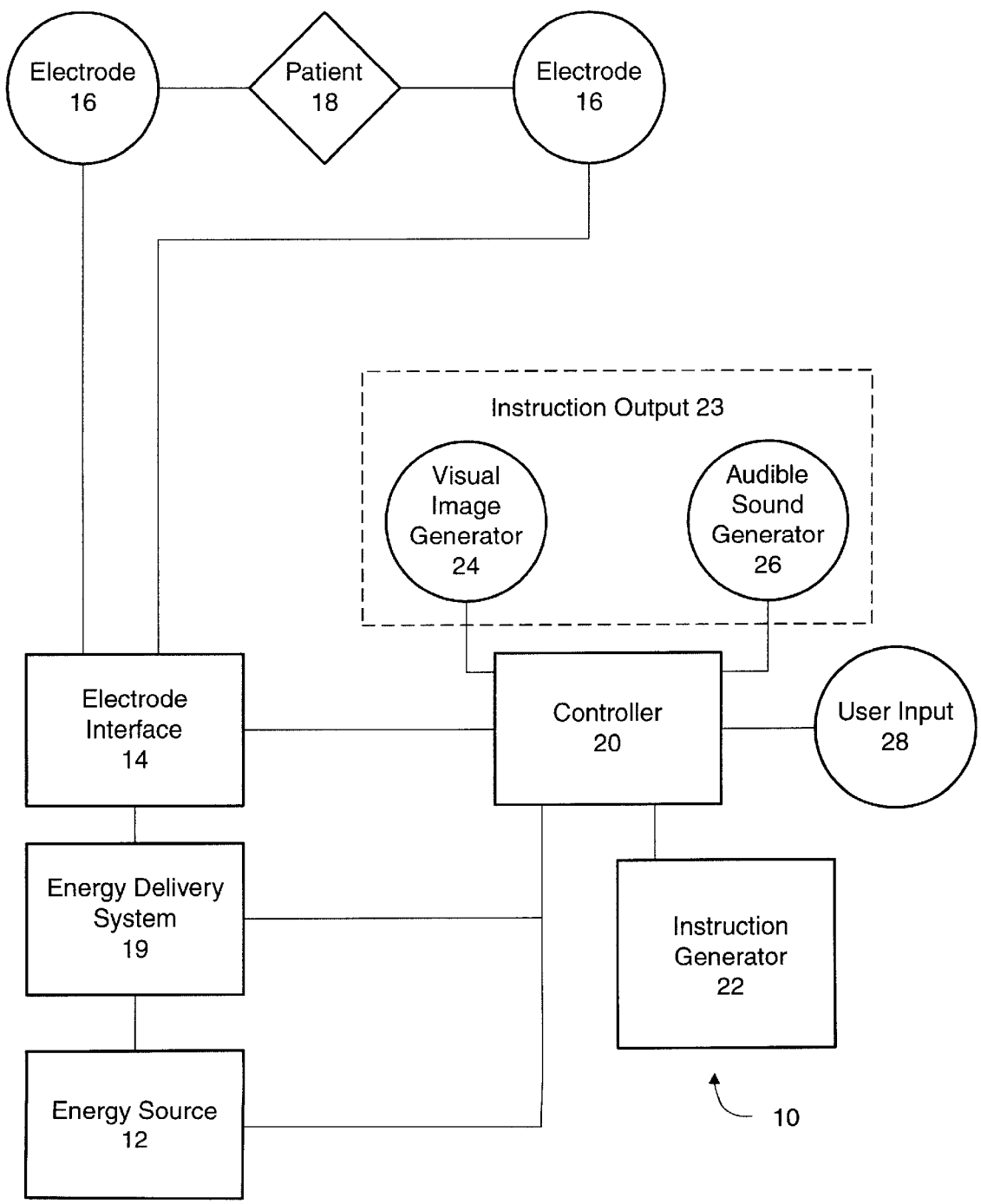
FIG. 1 is a diagrammatic representation of a defibrillator system.

FIG. 1 is a schematic block diagram of a defibrillator system 10 according to a preferred embodiment of this invention. The defibrillator system 10 comprises an energy source 12 to provide voltage or current pulses. A controller 20 operates an electrode delivery system 19 to selectively connect and disconnect energy source 12 to and from a pair of electrodes 16 electrically attached to a patient 18 through an electrode interface 14 to provide electrotherapy to the patient. The defibrillator system 10 may be a manual defibrillator or AED. Alternatively, defibrillator system 10 may be a defibrillator trainer that simulates the behavior of a manual or automatic/semi-automatic defibrillator in use, in which case the electrode interface and energy delivery system may be omitted.

In addition, controller 20 performs a protocol using information from an instruction generator 22. The controller 20 and instruction generator 22 determine the language of the defibrillator instructions based on information from the user. The instruction generator 22 may include a memory device such as FLASH, EEPROM, ROM or RAM containing software code used to generate visual and audible instructions. Instruction generator 22 may also include a gate array or other control logic.

The instructions may be delivered via an instruction output 23, which consists in this embodiment of a visual image generator 24 and an audible sound generator 26. Visual image generator 24 may display, among other things, commands to the user (either written or graphic representations). The visual image generator 24 may be, for example, a liquid crystal display ("LCD"). Additionally, an audible sound generator 26 may be provided that broadcasts audible commands from the instruction generator 22. Audible commands include verbal commands directing the user in the operation of the defibrillator 10. Activation of the visual image generator 24 and the audible sound generator 26 is controlled by the controller 20 in response to the information received from the instruction generator 22.

Additionally, user input 28 may be provided to interact with the instruction generator 22 to select the desired language of defibrillator operating instructions. In the embodiment shown in FIG. 1, the user input 28 interacts with the instruction generator 22 via controller 20. The user input may interact directly with the instruction generator in other embodiments.

Figure 2:
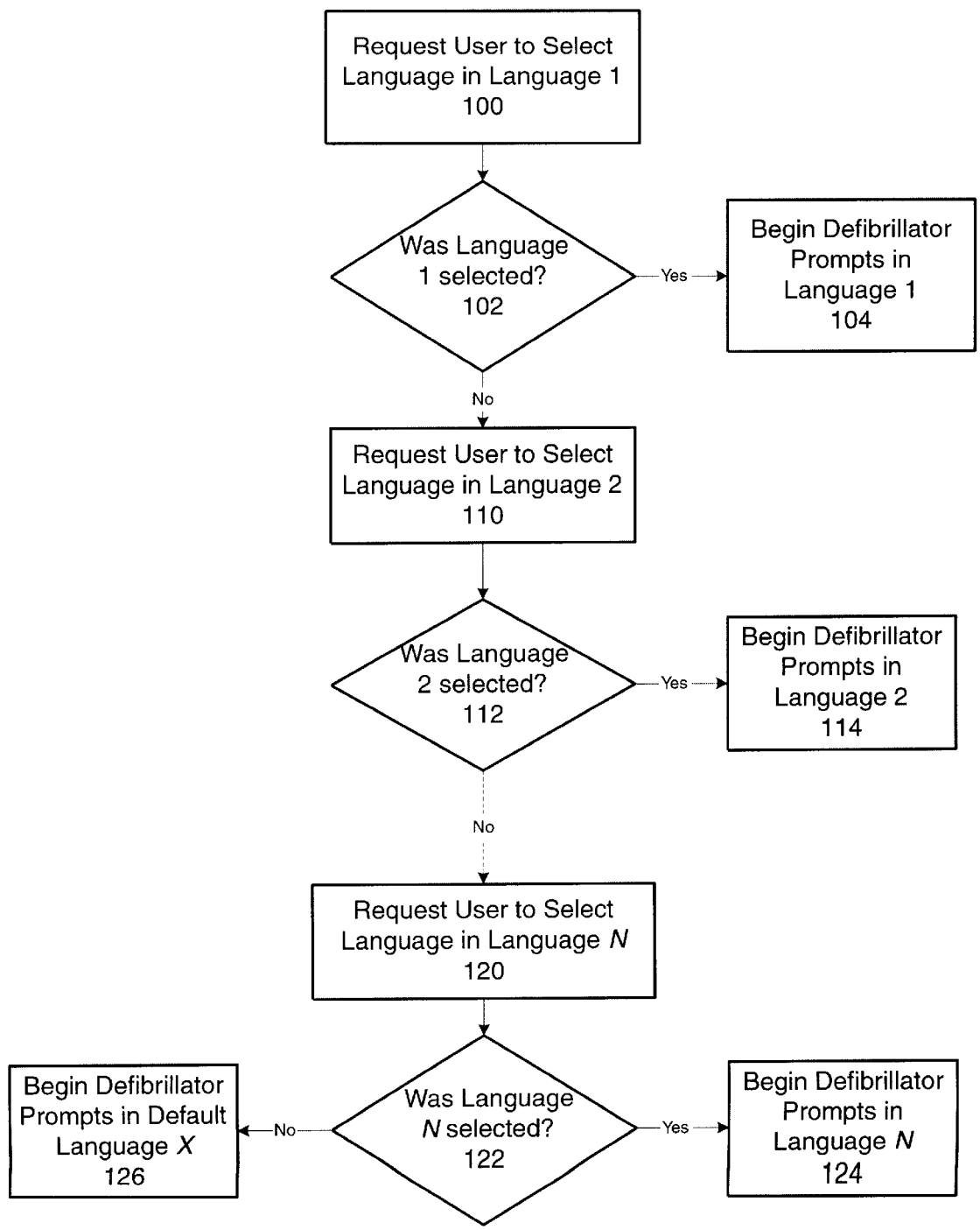
FIG. 2 is a flow chart demonstrating a defibrillator operating according to the current invention wherein the user selects a preferred language.

FIG. 2 is an example of a defibrillator operation method according to this invention. Using prompts in language "1", where language "1" is the first language that the prompts are delivered in, the defibrillator requests the user to select the language 100. The request may be audible, visual (on the display), or a combination of the two. If language "1" is selected 102, the defibrillator begins prompting the user in the procedures to deploy and use the defibrillator in language "1" 104.

If the user does not select language "1" 102, then the defibrillator requests the user to select a language in language "2" 110, where language "2" is the second language that the prompts are delivered in. Again, if language "2" is selected 112, then the defibrillator begins prompting the user in the procedures to deploy and use the defibrillator in language "2" 114.

If the user does not select language "2", the defibrillator continues to request the user to select a language in each of the languages designated during the set-up until the defibrillator reaches language N 120, where N is the number of languages that have been loaded into the defibrillator memory and designated during language prompt set-up. Once the defibrillator reaches language N 120, the defibrillator makes its final request for language selection from the user. If language N is selected, then the defibrillator will begin prompting the user in the procedures to deploy and use the defibrillator in the selected language.

If, however, the language N, or any previous language, has not been selected, the defibrillator begins prompting the user in the procedures to deploy and use the defibrillator in the default language X 126, where X is the language that has been designated as the default language for the defibrillator. The defibrillator may be programmed so that it reverts to the default language after passage of a specific amount of time. For example, if the defibrillator reaches language N, the defibrillator could request the user to select language N and if there is no response within, for example, 5–30 seconds, the defibrillator could begin prompting in the default language X In one embodiment, prior to deploying the defibrillator, i.e. prior to placing the defibrillator into service so that it is available for immediate use during an emergency, the defibrillator has prompts installed in the languages that will be needed in the location where the defibrillator is placed into service. Each installed language can be assigned a priority number. One of the installed languages will be identified as the default language.

For example, in Quebec N could be two languages, where French is language 1 and English is language 2. The priority of the languages could be set so that French is followed by English, with the default language being French. It is important to note, however, that the default language need not be the first prompting language. So, for example, for the same defibrillator in Quebec, where French is the first language, and English is the second language, the default language could be set at English.

In another example, such as in Europe, N could be three languages, where French is language 1, German is language 2 and English is language 3. Again, the default language could be set to be of the three languages.

In another embodiment, prior to deploying the defibrillator, the defibrillator will have prompts installed in several, or all, languages. Each language is assigned an identifier, such as a number, so that the prompts, once selected, can be quickly retrieved from memory. Each defibrillator is then programmed, or set-up, to prompt only for the languages selected during the set-up. The languages selected for prompting could be all or less than all of the languages available in the defibrillator's memory. An example of a language table that might be used is show in Table 1.

TABLE 1

| Language ID | Language Name |
|---|---|
| 01 | English |
| 02 | British English |
| 03 | Canadian English |
| 04 | Australian English |
| 05 | French |
| 06 | Canadian French |
| 07 | German |
| 08 | Italian |
| 09 | Spanish |

For example, in Quebec Canada a defibrillator could have prompts in all of the languages shown in Table 1 installed in memory, but be programmed to ask the user for the language prompt in Canadian English (03) and in Canadian French (06) only. The priority of the languages could be set so that Canadian French (06) is first, followed by Canadian English (03), with a default of Canadian French (06). As with the previous embodiment, the default language need not be the first language the defibrillator is programmed to use in requesting language selection. A more detailed example of such a language table is shown in Table 2.

TABLE 2

| Default | Sequence | Language ID | Language Name |
|---|---|---|---|
|  |  | 01 | English |
|  |  | 02 | British English |
|  | 1 | 03 | Canadian English |
|  |  | 04 | Australian English |
|  |  | 05 | French |
| ✓ | 2 | 06 | Canadian French |
|  |  | 07 | German |
|  |  | 08 | Italian |
|  |  | 09 | Spanish |

It is important to note that neither Table 1 nor Table 2 is an exhaustive list of languages; they are merely provided for illustration purposes.

As illustrated in Table 2, the designation of "1" and "2" for the language selection is typically independent of the language ID, and is used primarily to indicate the sequence of the language prompt. Other means of indicating order, such as "A", "B", "C" can be used without departing from the scope of the invention. It should be noted, as well, that the number designating order could, in some or all instances, also correlate to the language ID number. In such cases, the language ID and the priority can be combined into a single designation without departing from the scope of the invention.

In a typical embodiment of the invention shown in FIG. 2, a defibrillator will be set-up to prompt the user in two to six languages; the defibrillator may, however, be set-up to prompt the user in more than six languages in some instances.

Figure 3:
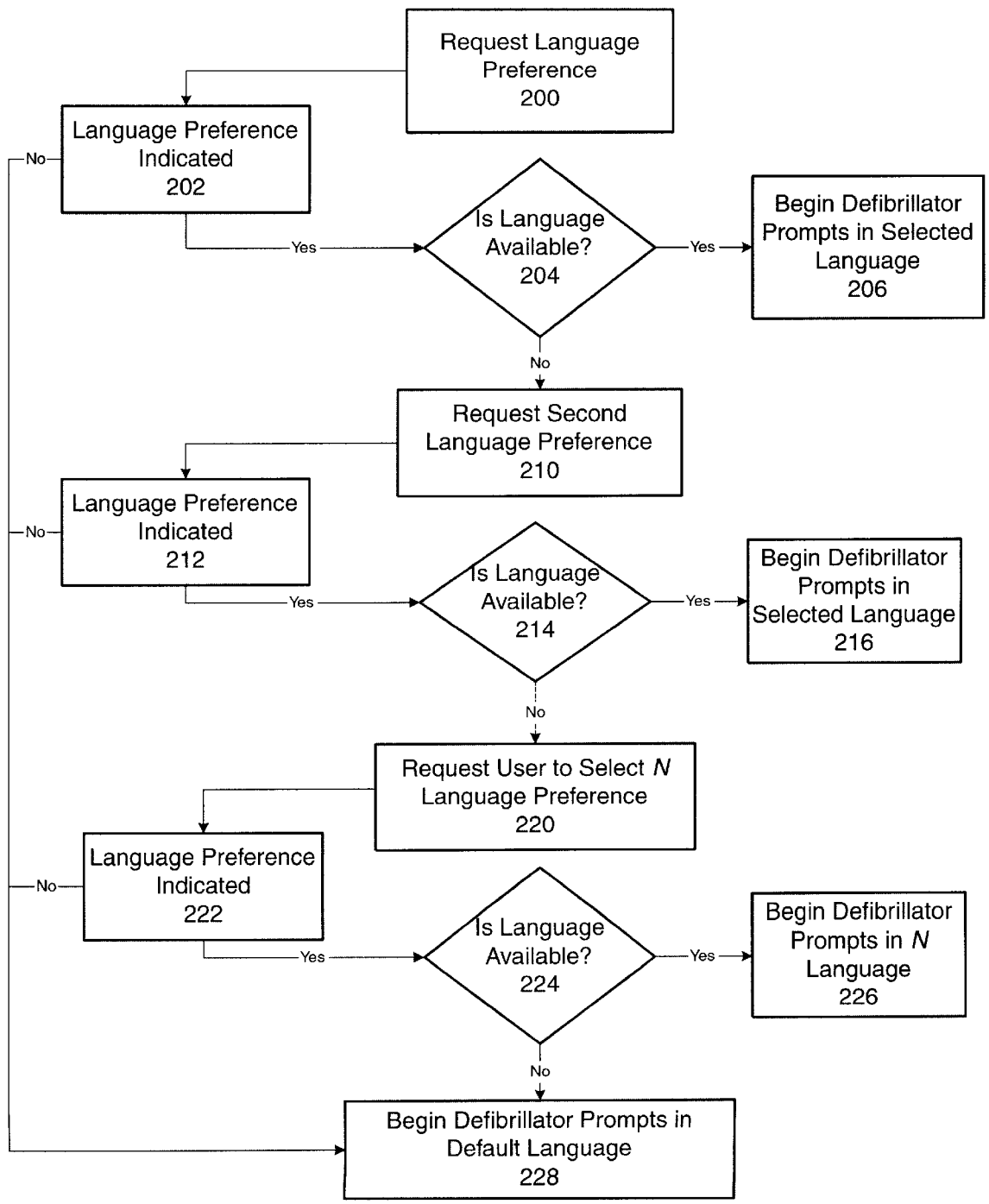
FIG. 3 is a flow chart demonstrating a defibrillator operating according to an alternate embodiment of the invention shown in FIG. 2.

FIG. 3 shows a method of operating a defibrillator according to an alternative embodiment of this invention. The defibrillator requests the user to indicate a language preference 200. Such a request may be made by, for example, displaying, either simultaneously or sequentially, the phrase "select language" or "indicate language preference" in a number of languages. The display may, alternatively, show only a list of the names of the languages in the language. Alternatively, the request may be made by, for example, an audible request to "select language" or "indicate language preference" sequentially in a number of languages. The request may also be made by a combination of audible and visual means.

The user then selects a language 202. The user may select the language by using, for example, buttons on the defibrillator or other input devices to scroll through the list of available languages (listed either simultaneously or sequentially on the visual display as described above) until the desired language is high-lighted. Each language shown would appear named in the language it represents. For example, Spanish would appear as "Español". Thereafter, the user would, for example, press another button to select the language.

Once the user selects a language 202, the defibrillator looks at the languages available in memory to determine whether or not the selected language is available 204. If the language is available, then the defibrillator begins prompting the user in the procedures to deploy and use the defibrillator in the selected language 206. If the selected language is not available, then the defibrillator displays a message indicating that the language is "not available" and requests the user to select a second language preference 210. The "not available," or equivalent message indicating that the language selected is unavailable, can be displayed visually, or can be audibly generated, or a combination of the two. Such visual display can be a graphic indication (such as the international NO symbol "Ø", a flashing or solid hand, or a flashing or solid "X") or a text indication. Where a text indication is used, one or more languages can be used to convey the message to the user prior to requesting the user to select a next language. A more detailed example of a language table that would be used in this embodiment is shown in Table 3.

TABLE 3

| Avail-able | Dis-play | Default | Sequence | Language ID | Screen Display | Language Name |
|---|---|---|---|---|---|---|
| YES | YES | ✓ | 1 | 01 | English | English |
| NO | YES |  |  | 02 | British English | British English |
| NO | NO |  |  | 03 | Canadian English | Canadian English |
| NO | NO |  |  | 04 | Australian English | Australian English |
| YES | YES |  | 2 | 05 | Français | French |
| NO | NO |  |  | 06 | Français Canadien | Canadian French |
| YES | YES |  | 3 | 07 | Deutsch | German |
| YES | YES |  | 4 | 08 | Italiano | Italian |
| YES | YES |  | 5 | 09 | Español | Spanish |

Once the user selects a second language 212, the defibrillator looks at the languages available in memory to determine whether or not the selected language is available 214. If the language is available, then the defibrillator begins prompting the user in the procedures to deploy and use the defibrillator in the selected language 216. If the selected language is not available, then the defibrillator displays a message indicating that the language is "not available" and requests the user to select another or "next" language 220.

Once the user selects the N language 222, where N is the highest number of times that the defibrillator has been set-up to ask for a language selection. The defibrillator then looks at the languages available in memory to determine whether or not the selected language is available 224. If the language is available, then the defibrillator begins prompting the user in the procedures to deploy and use the defibrillator in the selected language 226. If the selected language is not available, then the defibrillator begins prompting the user in the procedures to deploy and use the defibrillator in the default language 228.

Turning to a specific example, using the information shown in Table 3, the defibrillator has been loaded with 6 languages. The languages displayed on the screen are: English, British English, French, German, Italian and Spanish. The only languages that are actually available in memory, however, are: English, French, German, Italian and Spanish. In this instance, if a user were to select "British English" which is displayed as an option, but is not available, the user would receive a message advising the user that British English was not available. In a preferred embodiment, however, only languages that were available for selection would actually be displayed as viable options to the user to avoid such an error message.

The defibrillator would continue to prompt the user for a language selection N times. Note that N does not necessarily correlate to the number of languages added into memory. For example, N could be 3. In that instance, if after 3 selections, the user has not requested an available language (such as where the user continues to request British English, which is not available), the defibrillator would automatically begin prompting the user in the default language. Using the information provided in Table 3, the defibrillator would begin to prompt in English. Another advantage of this design is that it allows the user to dynamically make language selections. For example, a first tier responder can select a language with which he or she has increased proficiency. Thereafter, when the second tier responder arrives he or she may change the language selection, if appropriate, to correspond with their language proficiency.

Figure 4A:
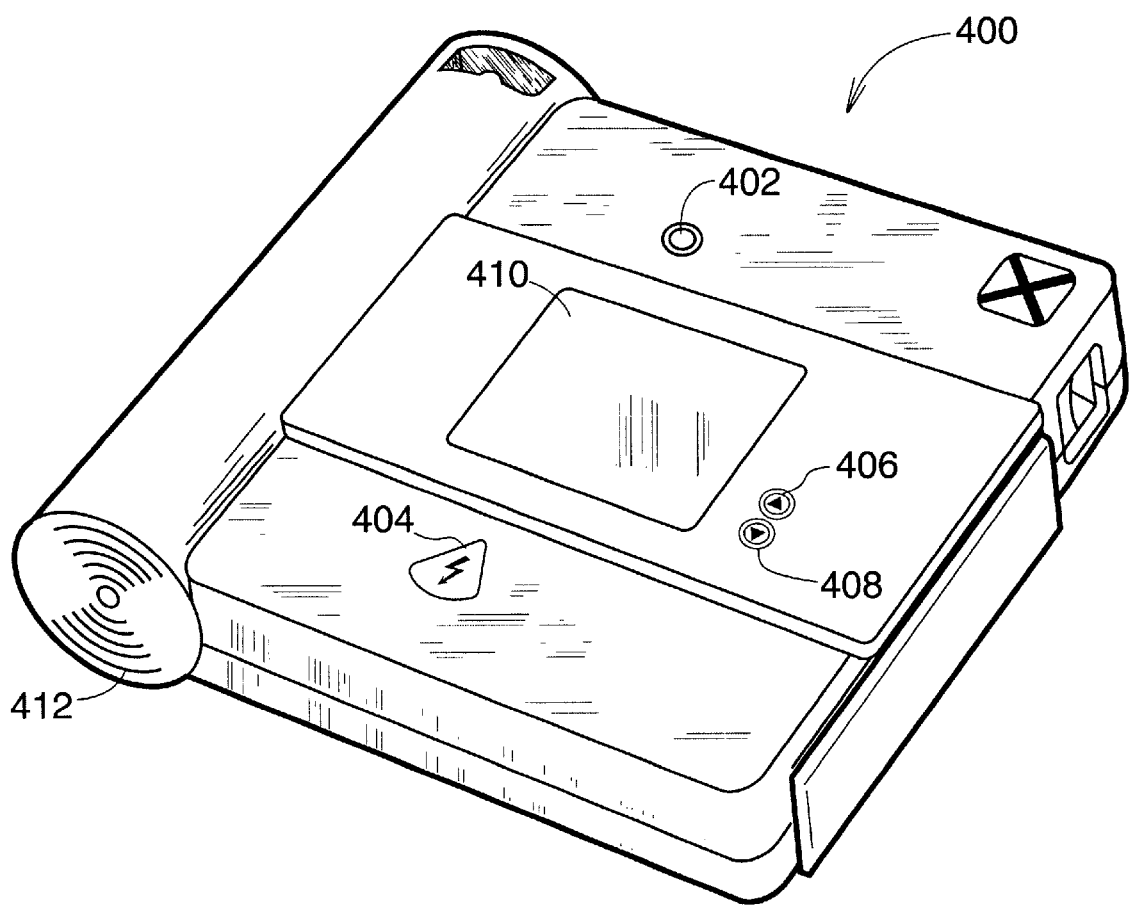
FIGS. 4A and 4B are a top elevational view of a defibrillator for use with this invention.

In a preferred embodiment, the invention is incorporated into the Heartstream FORERUNNER® AED. As shown in FIG. 4A, the FORERUNNER AED 400 has four user inputs: an on/off or power button 402; a shock button 404; and two display contrast buttons 406 and 408. An LCD 410 provides text and/or graphic display and a speaker 412 provides audio output.

Figure 4B:
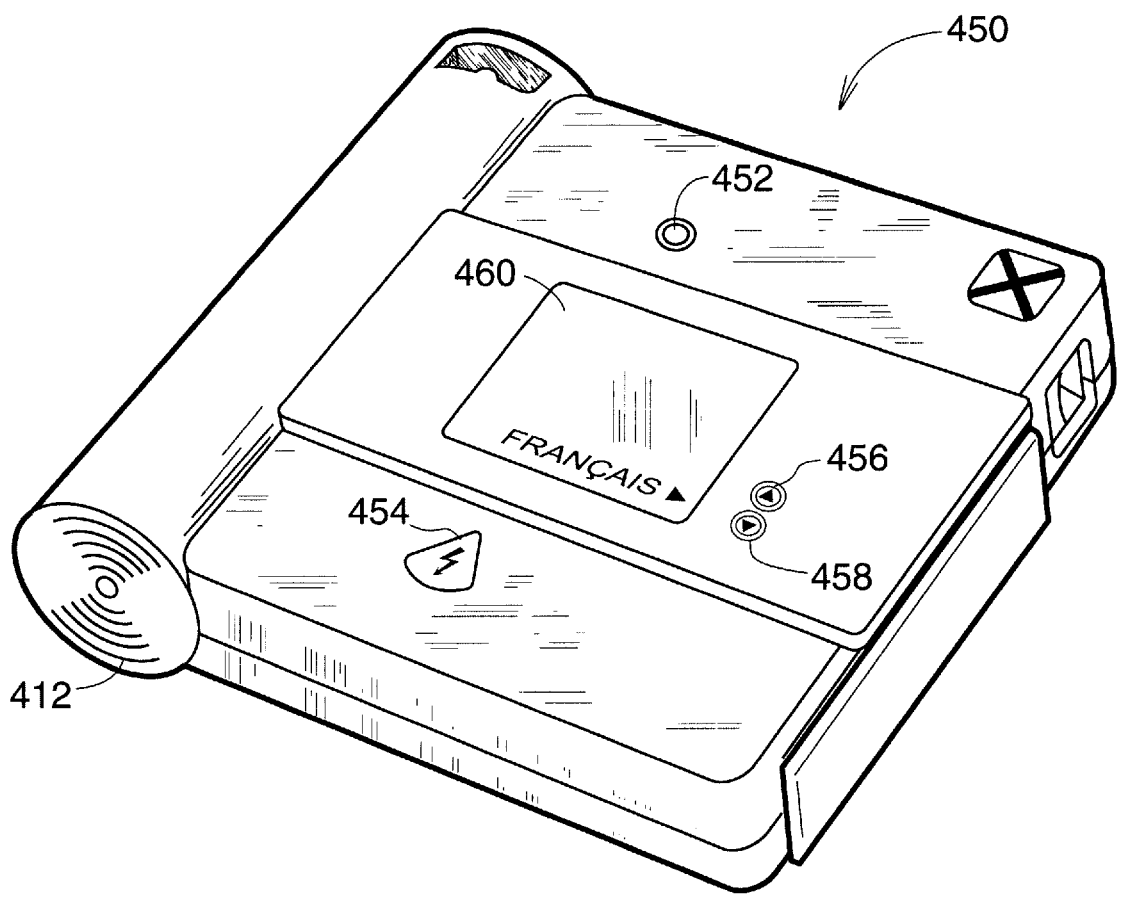

In operation, the display 410 could list one or more languages, and the user could use the contrast button 408 to scroll through the list until the desired language is high lighted. Thereafter, the user could use, for example, the up contrast button 406 to actually select the language. The instructions would then be visible on the display 410 or audible through the speaker 412, or a combination thereof Additionally, if the defibrillator was relying on voice instructions from the user (as discussed below), the phenomes would be received through the microphone (not shown in FIGS. 4A or 4B).

Figure 5:
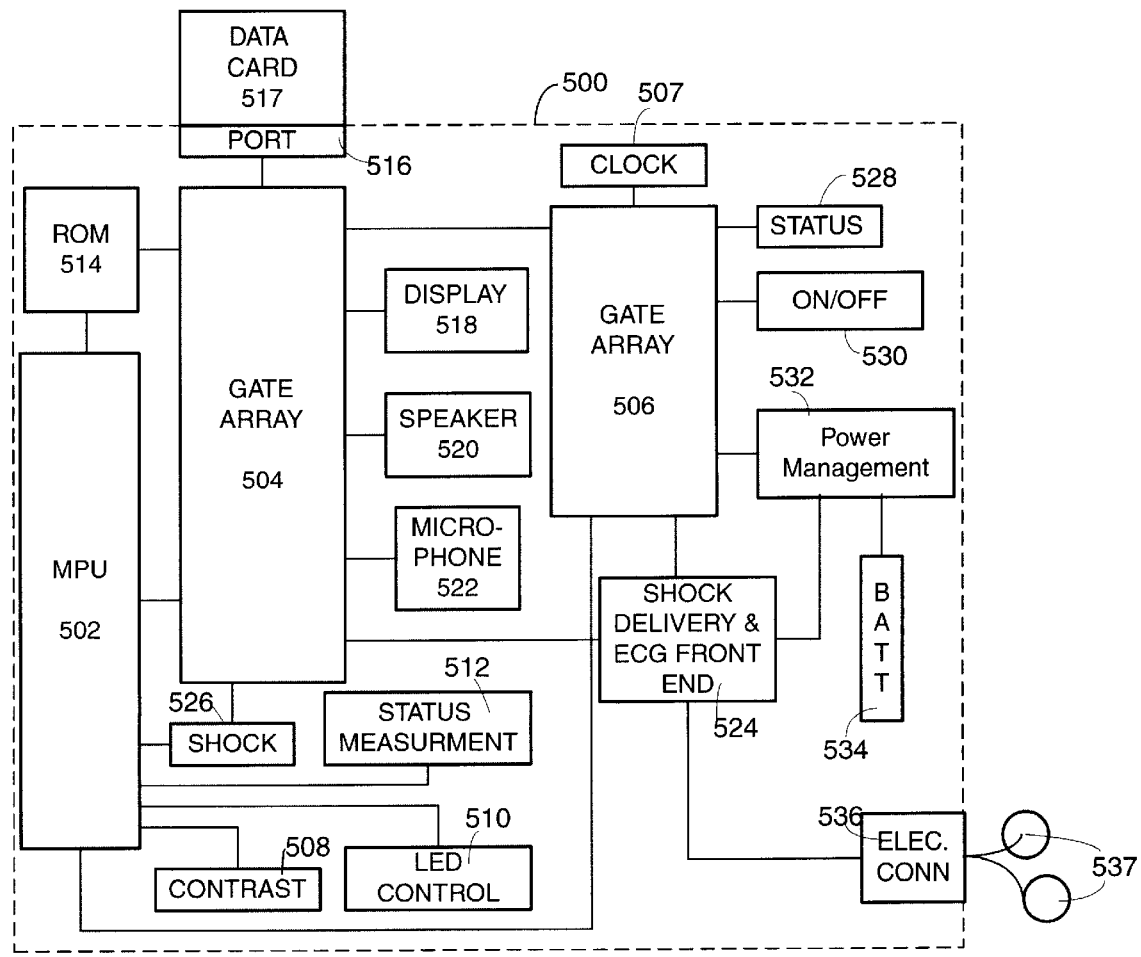
FIG. 5 is a schematic diagram of an external defibrillator for use with this invention.

FIG. 5 is a schematic representation of some internal components of the FORERUNNER AED 400 shown in FIG. 4A. AED control functions are divided among a microprocessor unit (MPU) 502 and two custom gate arrays 504 and 506. For example, MPU 502 controls the functions of contrast buttons 506 and 508, as shown by block 508 in FIG. 5, while gate array 504 controls LCD 410 and speaker 412, as shown by blocks 518 and 520 in FIG. 5. Further details regarding the remaining components of FIG. 5 may be found in U.S. Pat. No. 5,749,913, the disclosure of which is incorporated herein by reference.

In an alternative method of selecting language, a multiplicity of additional language specific buttons may be provided on the defibrillator which are each labeled with a single language. For example, a defibrillator could have two additional buttons labeled "Français" and "English" which the user would press to select prompts in either French or English. In operation, the language selection could be changed at any time during operation of the defibrillator to another language simply by pressing the desired language button. So, for example, if the defibrillator was a bilingual defibrillator with French and English a user could easily switch between the two languages by pressing the corresponding language button. This would be particularly advantageous in a situation where the first responder was, for example, proficient in English and the second tier responder was, for example, proficient in French because the language operation could be changed seamlessly without interrupting the operation of the defibrillator.

Alternatively, a "smart" button could be provided which has an LCD display on the button. The LCD could be used to reflect the language selection. In another embodiment, a "soft key" could be provided such as contrast button 458 shown in FIG. 4B. Where a soft key is used, the language selected could remain displayed on the screen 460, with an arrow pointing to the key that is functioning as a "soft key" 458. In the event, the user wishes to change the language selection, the user would press the button indicated by the display (in this case 458) to activate the language selection software. Thereafter, the user could scroll through a list of available languages on the screen in order to make a new selection. It is important to note that the dynamic changing of the operation language need not interrupt defibrillator operation (which includes functioning of the patient analysis system).

In yet another alternative embodiment of selecting language, the user could state the name of the desired language, such as "Deutsch", "Français", "Español" or "English". The defibrillator would then use voice recognition software to translate the phonemes of the spoken response into a corresponding language selection. Translations systems and methods of translating speech are known in the art and are not discussed herein. (See, e.g., Linebarger, et al. U.S. Pat. No. 5,652,897; Pallakoffet al. U.S. Pat. No. 5,651,096; Rivers U.S. Pat. No. 5,615,301; Strong U.S. Pat. No. 5,613,036; and Chou U.S. Pat. No. 5,583,761).

Figure 6:
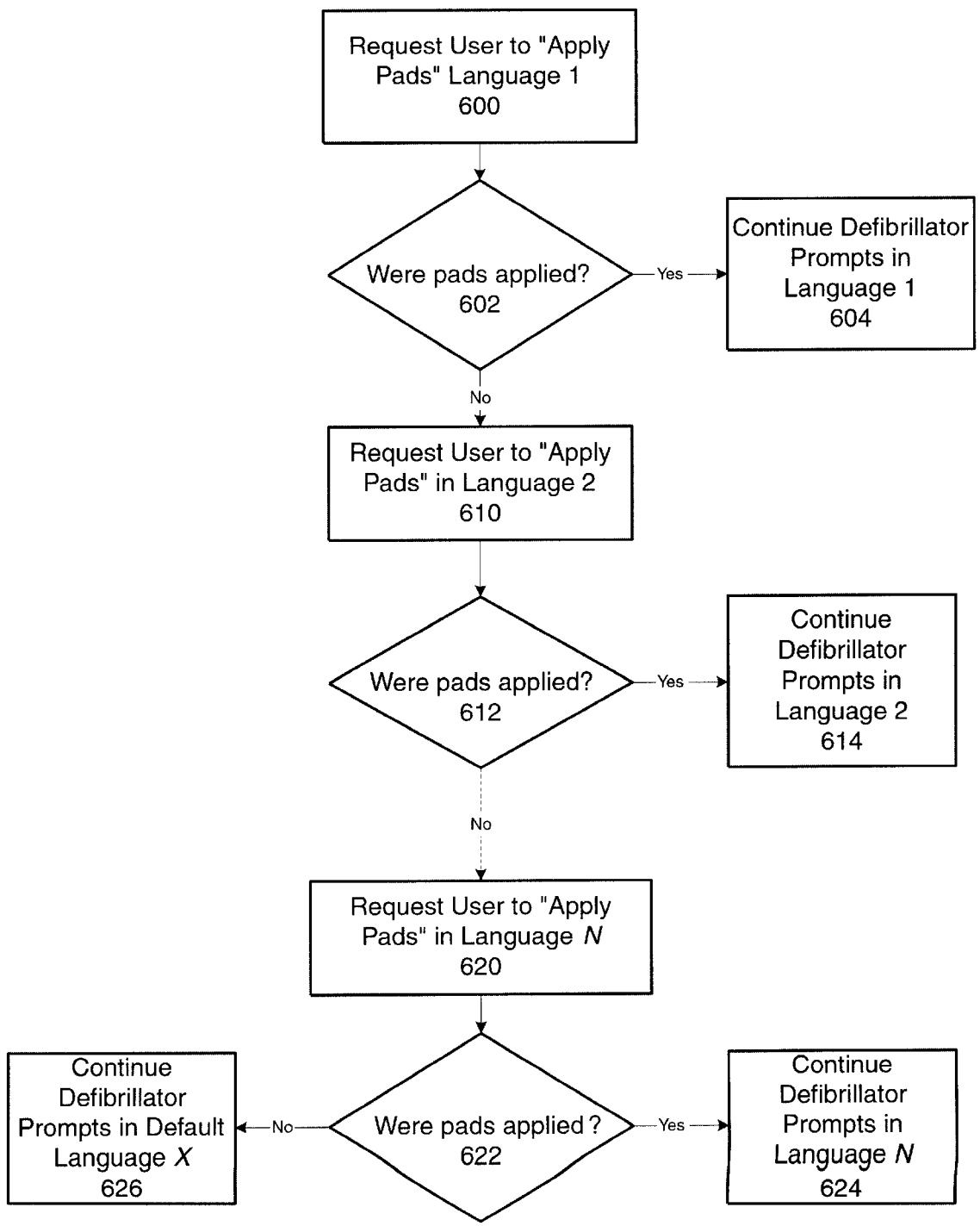
FIG. 6 is a schematic block diagram of a defibrillator operating according to an alternate embodiment wherein the defibrillator determines operation language based on user response to a command.

FIG. 6 shows an alternative embodiment wherein the defibrillator determines the prompt language from the user's response to instructions using the microprocessor to time the response. This is another example of how the defibrillator selects a prompt by using a result sensed by the machine. Using prompts in language 1, where language 1 is the first language that the prompts are delivered in, the defibrillator requests the user to, for example, "apply pads" 600. If the defibrillator detects that the pads have been applied following the prompt in language 1 and prior to the prompt in language 2, then the defibrillator will continue providing the remaining prompts in language 1 604.

If, on the other hand, the defibrillator does not detect that the pads have been applied within a reasonable amount of time, typically from 5 to 30 seconds, 602, the defibrillator will request the user to, for example, "apply pads" in language 2 610. If the defibrillator detects that pads have been applied following the prompt in language 2 and prior to the prompt in language 3, then the defibrillator will provide the remaining prompts in language 2 614.

If, however, the defibrillator does not detect that the pads have been applied within a reasonable amount of time, typically from 5 to 30 seconds, 612, the defibrillator will request the user to, for example, "apply pads" in language N 620. If the defibrillator determines that the pads were applied following the prompt in language N and prior to the prompt in language X then the defibrillator will continue prompting the user in language N 624. If the defibrillator does not detect that the pads have been attached following the prompt in language N, then the defibrillator will continue prompting the user in default language X 626.

The amount of time the defibrillator will wait before reverting to the default prompts can be set at the time language priorities are set in the defibrillator. As described above, if the user does not respond to the prompt within a reasonable amount of time, for example, 5 to 30 seconds, the defibrillator could begin prompting the user in a second language. More specifically, the defibrillator could prompt the user to "apply pads" in English. If the defibrillator does not detect that the pads have been applied, the defibrillator could then begin instructing the rescuer to "apply pads" in another language. The defibrillator could continue the prompting in different languages until the defibrillator detects that the pads have been attached. Once the defibrillator detects that the pads have been attached, the defibrillator will continue prompting the user to continue the operation of the defibrillator in the language used immediately prior to the pad connection. If during a later prompt the defibrillator provides an instruction which is not responded to, such as "deliver shock now, press the orange button", the defibrillator will again begin delivering the prompt in different languages with pauses in between to allow the user time to respond. In this situation, if the user spoke English, but due to nervousness did not respond to an "apply pads" command until after receiving the instruction to "apply pads" in, for example, Spanish, the user would then receive the later commands in Spanish. When the user failed to respond to the later command, the defibrillator would then begin cycling through the languages until a command in English was provided. In both situations, the defibrillator could be programmed to continue prompting in the default language once it has cycled through the available languages without a detected response.

As will be appreciated by those skilled in the art, "apply pads" need not be the first instruction provided to the user.

More specific examples of language order and default settings are described above and illustrated in Tables 1 through 3.

Figure 7:
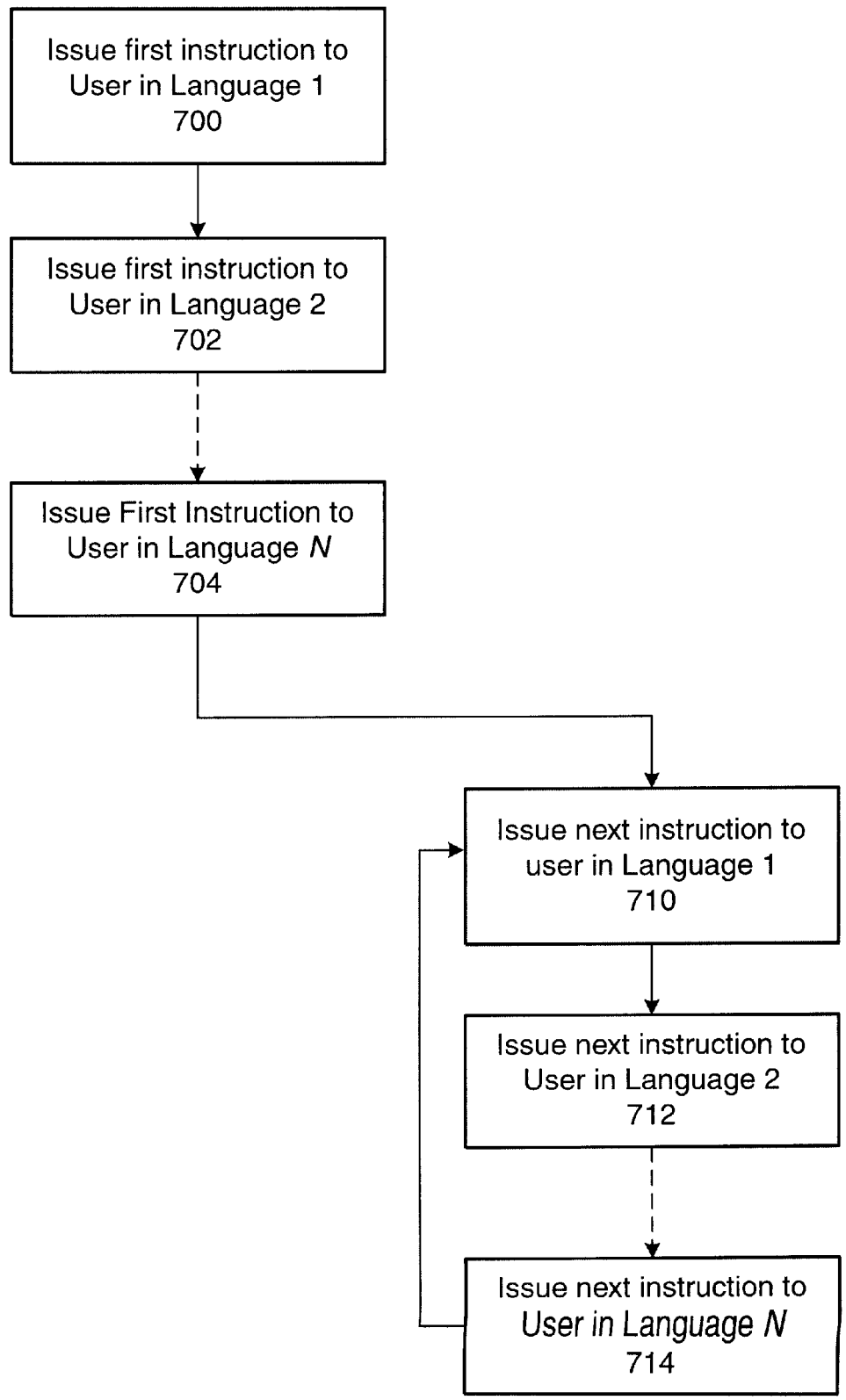
FIG. 7 is a flow chart demonstrating a defibrillator operating according to an alternate embodiment wherein the defibrillator delivers instructions in a multiplicity of languages sequentially.

FIG. 7 shows an alternative embodiment wherein the defibrillator operates in more than one language. Using prompts in language 1, where language 1 is the first language that the prompts are delivered in, the defibrillator requests the user to, for example, "apply pads" 700. Thereafter the defibrillator issues the same prompt in language 2 702. As will be appreciated by those of skill in the art, the prompts can be delivered with no pause between commands, or with a pause. If desired, the same prompt can be delivered in another language, up to N languages 704. However, ideally, the defibrillator will limit the number of prompt languages to no more than three in order to prevent a delay in defibrillation to the patient.

Following the issuance of the first instruction in a multiplicity of languages, the defibrillator will then instruct the rescuer in the next prompt in language 1 710, followed by the same prompt in language 2 712, followed by the same prompts in additional languages to language N 714. This sequential delivery of prompts in a multiplicity of languages continues throughout the operation of the defibrillator.

The examples described above in Tables 1 through 3 of language order and default settings are applicable to this invention as well.

Variations in the style of prompts are also encompassed in this invention. For example, the defibrillator could be set-up to deliver prompts in either a male voice, a female voice, or a computer generated voice. Additionally, the nature of the prompts can be changed to be either more or less commanding. For example, in English, "Deliver shock now" could be changed to "do me the favor of delivering the shock now" in another language, such as Japanese, where cultural considerations would require less commanding verbiage.

It should be appreciated that the scope of the invention is not limited to the embodiments described above. Various modifications and alterations might be made by those skilled in the art without departing from the spirit and scope of the present invention.

What is claimed is:

1. A method of selecting an operation language of an external defibrillator comprising:
   prompting a defibrillator operator to select a language in a first language from a plurality of languages;
   receiving the language selection from the operator;
   determining whether the selection is available in memory; and
   using the first language to provide instructions to the operator if the selection is determined to be available in memory when deploying the defibrillator for use on a patient.

2. The method of claim 1 wherein the step of using the first language to provide instructions further comprises displaying the language visually.

3. The method of claim 2 wherein the step of prompting the defibrillator operator further comprises displaying a graphical prompt to the user to select the first language.

4. The method of claim 1 wherein the step of using the first language to provide instructions further comprises announcing the language audibly.

5. The method of claim 1 further comprising the step of:
   prompting the defibrillator operator to select a language in a second language if the first language is determined not to be available in memory.

6. The method of claim 5 further comprising the step of determining whether the second prompting language is available in memory.

7. The method of claim 6 further comprising using the second language to provide instructions to the operator if the selection is determined to be available in memory.

8. The method of claim 7 further comprising the step of:
   prompting the defibrillator operator to select a language in a third language if the second language is determined not to be available in memory.

9. The method of claim 8 further comprising the step of determining whether the third prompting language is available in memory.

10. The method of claim 9 further comprising using the third language to provide instructions to the operator if the selection is determined to be available in memory.

11. The method of claim 1 further comprising the step of delivering prompts in a default language if a selection is not made by the operator.

12. The method of claim 11 wherein the step of prompting the defibrillator further comprises displaying a graphical prompt to the user to select the first language.

13. The method of claim 1 wherein the step of prompting the defibrillator operator further comprises delivering audible prompts from an audible sound generator.

* * * * *